United States Patent [19]

Nordenström et al.

[11] 4,289,135
[45] Sep. 15, 1981

[54] APPARATUS FOR DESTROYING A SELECTED PART OF BIOLOGICAL TISSUE

[75] Inventors: Björn Nordenström, Rönninge; Jerker Olsson, Bandhagen, both of Sweden

[73] Assignee: Tekniska Rontgencentralen AB, Sweden

[21] Appl. No.: 95,420

[22] Filed: Nov. 19, 1979

[30] Foreign Application Priority Data

Nov. 23, 1978 [SE] Sweden .............................. 7812092

[51] Int. Cl.³ .............................................. A61N 1/20
[52] U.S. Cl. ............................................. 128/419 R
[58] Field of Search ................. 128/419R, 783, 804, 128/303.13, 303.14, 303.17, 303.18, 42 D, 421; 250/372

[56] References Cited

U.S. PATENT DOCUMENTS

| | | | |
|---|---|---|---|
| 3,710,115 | 1/1973 | Jubb ................................. | 250/372 |
| 3,851,970 | 12/1974 | Adler et al. ..................... | 250/372 X |
| 4,016,886 | 4/1977 | Doss et al. ...................... | 128/804 X |
| 4,114,623 | 9/1978 | Meinke et al. .................. | 128/303.14 |
| 4,141,359 | 2/1979 | Jacobsen et al. ........... | 128/419 R X |
| 4,184,492 | 1/1980 | Meinke et al. ................ | 128/303.14 |
| 4,188,927 | 2/1980 | Harris ............................. | 128/303.14 |

FOREIGN PATENT DOCUMENTS

| | | | |
|---|---|---|---|
| 311660 | 5/1929 | United Kingdom ............... | 128/783 |
| 855459 | 11/1960 | United Kingdom .......... | 128/303.17 |

Primary Examiner—Lee S. Cohen
Attorney, Agent, or Firm—Kinzer, Plyer, Dorn & McEachran

[57] ABSTRACT

An apparatus for destroying a neoplasm, such as a tumor, including electrodes (9,12) connected to a source (1) of direct voltage, of which electrodes one (9) is intended to be arranged in the neoplasm (16) and the other to be brought into electrically conductive contact with the body tissue (17) at a distance from said neoplasm. Measuring apparatus (7) is provided for measuring and indicating the current flowing between the electrodes and integrating apparatus (14) is provided for time integrating the measured current and indicating the electrical charge applied to said neoplasm and said body tissue.

5 Claims, 2 Drawing Figures

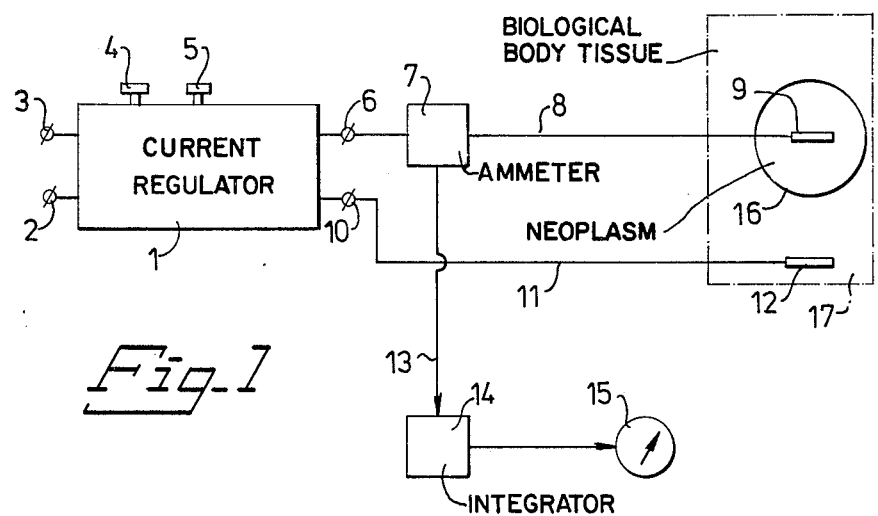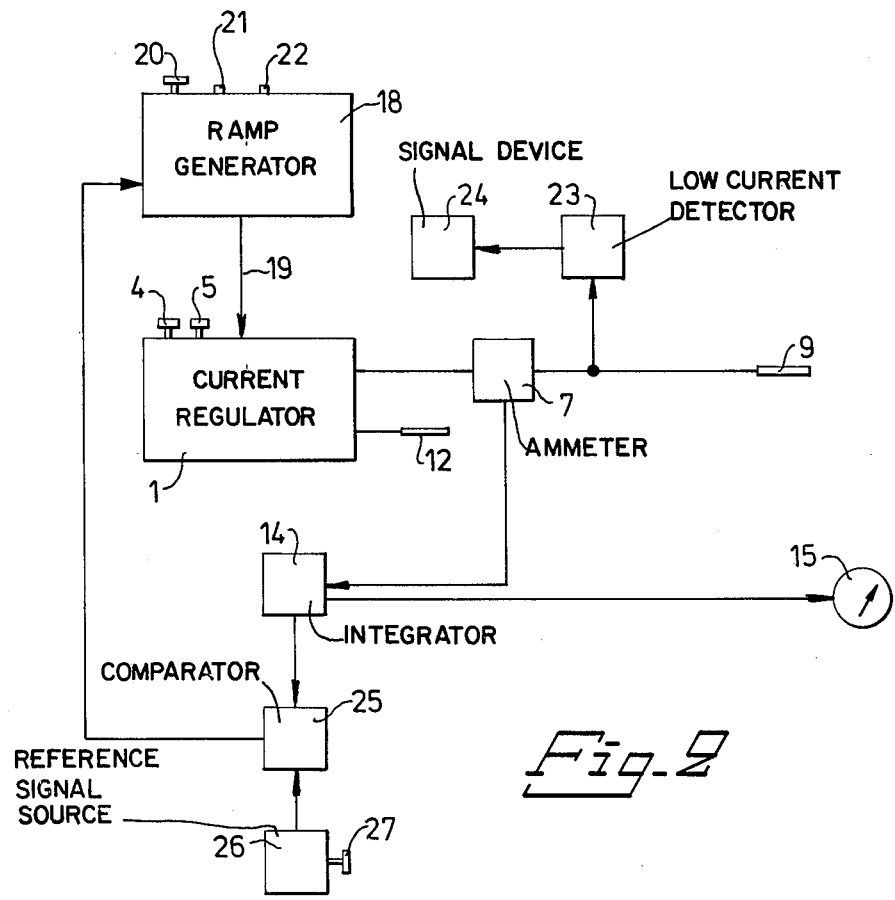

APPARATUS FOR DESTROYING A SELECTED PART OF BIOLOGICAL TISSUE

The present invention relates to an apparatus for destroying a selected part of body tissue, e.g. a neoplasm, such as a tumour, in biological body tissue, using at least two electrodes connected to a direct voltage source, of which electrodes one is intended to be introduced completely or partially into said neoplasm and to be connected to one pole of said voltage source, and the other of said electrodes is intended to be brought into electric contact with said body tissue at a distance from said neoplasm.

Such an apparatus has been used to greatly heat and/or to burn the neoplasm to be destroyed, by producing a high power input, although in certain cases this technique of heating said neoplasm is completely unsuitable and may cause harmful damage.

Consequently a prime object of the present invention is to provide an apparatus by means of which neoplasms can be destroyed without generating appreciable quantities of heat, and by means of which such neoplasms as tumours can be treated with the least possible damage to surrounding, healthy tissue.

This object is realized with the apparatus defined in the accompanying claims and based on the discovery that tissue can be destroyed by ionization with the aid of electrolysis. The effect is dependent partly on the voltage level and partly on the amount of charge, expressed in ampere-seconds, which passes the tissue between the electrodes.

The novel apparatus is substantially characterized in that measuring means are provided for measuring and indicating the current flowing between the electrodes and for interrupting the supply of current to the electrodes from the direct voltage source, when the current exceeds a given value at a given voltage; and in that integrating means are provided for the time-integration of the current flowing between the electrodes and for indicating the electrical charge applied to the neoplasm and the body tissue.

Conveniently, the source of direct voltage is arranged to deliver a determined highest current and a determined highest voltage.

Means may also be provided for breaking the supply of current to the electrodes when the integrating circuit indicates that a given charge has been reached.

The means for interrupting the supply of current may comprise a signal comparison circuit (25) arranged to receive a signal from the integrating circuit (14), which signal indicates the momentary charge in the body tissue, and a reference signal indicating a desired end charge in the body tissue, from a reference signal circuit (26).

Conveniently a time-constant circuit (18) is arranged to control the voltage source in a manner such that current and/or voltage to the electrodes follows a selectable time-constant curve.

Other characterizing features of the invention are disclosed in the claims and the following description.

Two exemplary embodiments of the invention will now be described with reference to the accompanying drawing, in which FIG. 1 is a block schematic of an apparatus according to the invention, and FIG. 2 is a block schematic of another apparatus according to the invention.

FIG. 1 illustrates a device 1 for generating current at a given, selected maximum strength. The device is supplied from the main supply or from batteries, via input terminals 2, 3. The voltage selected for the treatment process, e.g. 10 volts, is set by means of a knob 4 arranged, for example, to activate a voltage regulator (not shown) in the device 1. A desired maximum current, e.g. 20 mA, is selected by means of a knob 5. Connected to the output terminal 6 of the device 1 is a current, measuring circuit 7, which in its simplest form comprises an analogue or digital amperemeter, and the current measuring circuit 7 is connected to an electrode 9 via a conductor 8. Connected to the other output terminal 10 of the device 1 via a conductor 11 is a second electrode 12. A signal corresponding to the strength of the current passing between the electrodes 9 and 12 and measured by the circuit 7 is fed to an integrating circuit 14 over a conductor 13, said circuit 14 being arranged to time-integrate the current and thus to form a value of the charge, expressed in ampereseconds or coulombs. The integrated circuit 14 transmits the value of the continuously measured charge to an analogue or digital indicator 15.

The electrode 9, which may comprise a thin platinum wire, is placed in a neoplasm or defined tissue portion 16, which neoplasm may consistute a lung tumour. The other electrode 12 is inserted into the biological body tissue 17 surrounding the neoplasm. The tissue between the two electrodes contains liquid and is therefore electrically conductive. When the cells in the neoplasm 16 are to be destroyed, the device 1 is connected to the main supply and the voltage set to the desired value by means of the knob 4, and the strength of the current is increased progressively from zero to a desired maximum value by means of the knob 5. It is assumed that the two knobs are provided with or cooperate with setting scales (not shown). The reason why the current is caused to increase slowly, is to avoid cramps and the like in the tissue. Initially, the current will lie far below the set maximum value. When the tumour cells are more electron-negatively charged than the surrounding cells, the positive electrode is preferably arranged into the tumour cells. It is assumed here that the neoplasm to be destroyed is electron-negative and that the electrode 9 is the positive electrode. The electron-negative cellular molecules within the tumour 16 will be ionized in the filed created between the electrodes 9 and 12, and as a result of the charge totally supplied to the tissue during the treatment period the tumour cells will decompose, simultaneously as water departs in a direction towards the negative electrode 12. The destroyed area of tissue around the electrode is approximately spherical when the electrode 9 is a short electrode, and transforms to a cylindrical configuration when the electrode is a long electrode. During tests on lung tissue, a section of tissue having a diameter of 30 mms when seen perpendicularly to the longitudinal axis of the electrode 9 was destroyed when applying a charge of 600 coulombs. The electrode, which was made of platinum, had a thickness of 0.2 mm. The treatment was continued for 4 hours and the current had a maximum strength of 40 mA. As beforementioned, there is also obtained an electrolysis, with resultant formation of chlorine at the positive electrode, said chlorine also contributing to the destruction of the tumour cells.

The requisite charge applied to the tissue between the electrodes must be empirically determined and when the instrument 15 shows that the desired charge has been reached, the voltage is reduced so that the current slowly falls to zero, or the set maximum current value is also slowly decreased.

FIG. 2 is a block schematic of a further embodiment of an apparatus according to the invention, the elements incorporated in the apparatus of FIG. 1 being identified with the same references.

The voltage device 1 is controlled in this case from a so-called ramp generator 18 arranged to produce a control signal on its output and to transmit said signal to the device 1, on an output conductor 19. This control signal has the form of a time-constant signal which, in accordance with a determined time constant, increases the voltage from the device 1 from zero to the maximum value set by means of the knob 4. The time constant of the ramp generator 18 is set by means of a knob 20 and the generator is also provided with a start button 21 for starting the control signal from the generator, and a stop button 22 for interrupting transmission of said control signal. When there is no control signal on the output conductor 19, the voltage device 1 is blocked and no current is supplied to the body tissue between the electrodes 9 and 12. The current-measuring circuit 7 is connected to a current-indicating circuit 23, which when the current measured by the circuit 7 falls, during the treatmentprocess, to zero or a low value which greatly deviates from the normal current, a warning signal is sent to a warning device 24, which may be an acoustic device, for example. When during the treatment process, the current falls abnormally, this indicates that gas has formed around an electrode, as a result of the electrolysis of water, and the treatment must then be interrupted until the gas bubbles disappear. The time-integrating circuit 7 sends its indicating signal to the indicator 15 and to a comparison circuit 25, which obtains a reference signal from a reference-signal emitter 26, which emitter can be set to a desired charge, e.g. 200 coulombs, by means of a knob 27. Thus, the comparator 25 receives the signal from the integrating circuit 14, indicating the charge applied to the body tissue between the electrodes at each moment in time, and a reference signal from the emitter 26, indicating the desired empirically determined charge. When the two signals coincide or when the signal from the integrated circuit indicates that the desired charge has been almost reached, the comparator 25 sends an end signal to the ramp generator 18, which changes its control signal to the device in a manner such that the voltage and current slowly decrease.

It has been stated in the aforegoing that the electrode located externally of the neoplasm is also inserted into the body tissue. In certain instances, such as when destroying a tumour in a woman's breast, this electrode is placed against the skin. In this case, the electrode is suitably given a wide surface, in order that the current density externally of the neoplasm to be destroyed is as low as possible. A contributory effect with regard to the destruction of neoplasms is that the blood in the blood vessels nearest the treatment site will coagulate, so that no oxygen is delivered to the cells.

The field obtained in the neoplasm or selected tissue-area to be destroyed can be used to advantage to concentrate cellular poisons, which accelerate the process of destruction in the neoplasm or said area of tissue. The cellular poisons have or are given the opposite polarity to the electrode in the neoplasm.

We claim:

1. An apparatus for destroying a neoplasm such as a tumor in a biological body tissue, said apparatus including at least two electrodes, means to connect said electrodes to a source of direct current, one of said electrodes arranged to be inserted in said neoplasm and the other arranged to be placed in electrically conductive contact with said body tissue at a distance from the neoplasm, current measuring means located between said source of direct current and one of said electrodes, integrating circuit means connected to said current measuring means for time-integrating the current passing between the electrodes, and an indicator connected to the integrating circuit means for indicating the total ampereseconds applied to the neoplasm and body tissue during a treatment period.

2. The apparatus of claim 1 in which means are provided to select the maximum voltage and maximum current which can be applied to the electrodes by the source of direct current.

3. The apparatus of claim 1 or claim 7 in which means are provided to interrupt the supply of direct current to the electrodes when the charge measured by the integrating circuit means reaches a selected value.

4. The apparatus of claim 3 in which said means to interrupt the direct current supply to the electrodes includes means to provide a reference signal indicative of a desired final charge in the body tissue, and means to receive a signal from the integrating circuit means indicating the actual charge in the body tissue and to compare the two signals and means connecting said signal comparison means with said source of direct current to interrupt the current from said source of direct current.

5. The apparatus of claim 1 in which the voltage applied by the source of direct current is controlled by a ramp generator to follow a selected time-constant curve.

* * * * *